(12) United States Patent
Etinger et al.

(10) Patent No.: US 6,849,737 B2
(45) Date of Patent: Feb. 1, 2005

(54) SYNTHESIS AND PURIFICATION OF VALACYCLOVIR

(75) Inventors: Marina Yu Etinger, Nesher (IL); Lev M. Yudovich, Haifa (IL); Michael Yuzefovich, Haifa (IL); Gennady A. Nisnevich, Haifa (IL); Ben Zion Dolitzky, Petach-Tiqva (IL); Boris Pertsikov, Nesher (IL); Boris Tishin, Haifa (IL); Dina Blasberger, Raanana (IL)

(73) Assignee: Teva Pharmaceutical Industries Ltd., Petah Tiqva (IL)

(*) Notice: Subject to any disclaimer, the term of this patent is extended or adjusted under 35 U.S.C. 154(b) by 0 days.

(21) Appl. No.: 10/293,347

(22) Filed: Nov. 13, 2002

(65) Prior Publication Data

US 2003/0153757 A1 Aug. 14, 2003

Related U.S. Application Data

(60) Provisional application No. 60/332,802, filed on Nov. 14, 2001, and provisional application No. 60/342,273, filed on Dec. 21, 2001.

(51) Int. Cl.[7] ..................... C07D 473/18; A61K 31/522
(52) U.S. Cl. ..................................................... 544/276
(58) Field of Search ..................... 544/276; 514/263.38

(56) References Cited

U.S. PATENT DOCUMENTS

| | | |
|---|---|---|
| 4,199,574 A | 4/1980 | Schaeffer |
| 4,957,924 A | 9/1990 | Beauchamp |
| 6,040,446 A * | 3/2000 | Dvorak et al. .............. 544/276 |
| 6,107,302 A * | 8/2000 | Carter et al. ........... 514/263.38 |
| 6,218,568 B1 | 4/2001 | Dvorak et al. |
| 2003/0114470 A1 * | 6/2003 | Wizel et al. ................ 544/276 |

FOREIGN PATENT DOCUMENTS

| | | | | |
|---|---|---|---|---|
| WO | WO 9725989 A1 * | 7/1997 | .......... | A61K/31/52 |
| WO | WO 9803553 A1 * | 1/1998 | ......... | C07D/473/00 |

OTHER PUBLICATIONS

Goodman & Gilman, The Pharmacological Basis of Therapeutics, 1193–1198 (9th ed. 1996).

* cited by examiner

*Primary Examiner*—Mark L. Berch
(74) *Attorney, Agent, or Firm*—Kenyon & Kenyon

(57) ABSTRACT

The present invention relates to protected valacyclovir, N-tert-butoxycarbonyl-L-valine 2-[(2-amino-1,6-dihydro-6-oxo-9H-purin-9-yl)methoxy] ethyl ester, and a method of making it. The present invention further relates to a method of making valacyclovir including the steps of coupling an amine protected valine selected from N-t-butoxycarbonyl valine and N-formyl valine with acyclovir using a coupling agent to form a protected valacyclovir, and deprotecting the protected valacyclovir to form valacyclovir or a pharmaceutically acceptable salt thereof. The present invention further relates to valacyclovir in pure form, a method of making pure valacyclovir, and to compositions containing pure valacyclovir.

24 Claims, No Drawings

SYNTHESIS AND PURIFICATION OF VALACYCLOVIR

CROSS REFERENCE TO RELATED APPLICATIONS

This application claims the benefit of U.S. provisional application Ser. No. 60/332,802, filed Nov. 14, 2001, and U.S. provisional application Ser. No. 60/342,273, filed Dec. 21, 2001, both of which are incorporated herein by reference.

FIELD OF THE INVENTION

The present invention relates to protected valacyclovir, N-tert-butoxycarbonyl-L-valine 2-[(2-amino-1,6-dihydro-6-oxo-9H-purin-9-yl)methoxy] ethyl ester, and a method of making it. The present also invention relates to a novel method of synthesis and purification of the antiviral compound valacyclovir hydrochloride. The present invention further relates to valacyclovir in pure form, a method of making pure valacyclovir, and to compositions containing pure valacyclovir.

BACKGROUND OF THE INVENTION

Valacyclovir is an L-valyl ester prodrug of acyclovir. Acyclovir, 6H-purin-6-one, 2-amino-1,9-dihydro-9-[(2-hydroxyethoxy)methyl], is a synthetic purine nucleoside analog derived from guanine, having the following chemical structure formula shown in FIG. I.

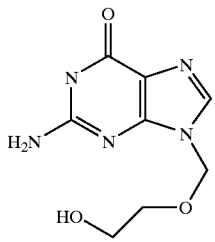

FIG. I

CAS Registry No. 59277-89-3

Acyclovir has been found to have high anti-viral activity and is widely used in the treatment and prophylaxis of viral infections in humans, particularly infections caused by the herpes group of viruses. See Goodman and Gilman's, *The Pharmacological Basis of Therapeutics*, 1193–1198 (9th ed. 1996). Acyclovir, as its sodium salt, is commercially available under the brand name Zovirax®. U.S. Pat. No. 4,199,574 discloses the treatment of viral infections with acyclovir.

Valacyclovir, L-valine, 2-[(2-amino-1,6-dihydro-6-oxo-9H-purin-9-yl)methoxy]ethyl ester, has the following chemical structure formula shown in FIG. II.

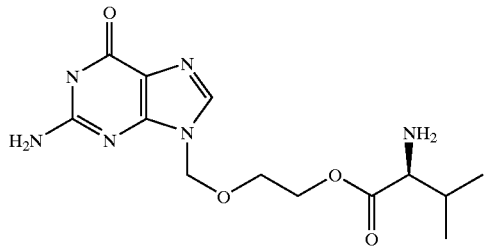

FIG. II

CAS Registry No. 124832-26-4

The U.S. Food and Drug Administration has approved valacyclovir for the treatment of herpes zoster and genital herpes. Valacyclovir hydrochloride is commercially available under the brand name Valtrex®.

For oral administration, it is more advantageous to administer valacyclovir rather than acyclovir because acyclovir is poorly absorbed from the gastrointestinal tract in both animals and humans. In contrast, valacyclovir is rapidly absorbed from the gastrointestinal tract after oral administration. Moreover, valacyclovir is converted rapidly to acyclovir after oral administration in healthy adults. The conversion of valacyclovir is thought to result from first-pass intestinal and hepatic metabolism through enzymatic hydrolysis.

U.S. Pat. No. 4,957,924 discloses amino acid esters of the purine nucleoside analog acyclovir, pharmaceutically acceptable salts thereof, and processes for the preparation of such compounds. Also disclosed are pharmaceutical formulations and the use of the disclosed compounds in the treatment of herpes virus infections. Valacyclovir and its salts, including the hydrochloride salt, are among the disclosed compounds.

In particular, the '924 patent discloses a method for preparing valacyclovir by condensation of a protected valine, wherein CBZ-valine, a catalytic amount of 4-dimethylaminopyridine, and dicyclohexylcarbodiimide, a coupling reagent, were added to a solution of acyclovir in dimethylformamide. The CBZ group was removed by catalytic hydrogenation, which requires using hydrogen gas and specialized equipment (e.g. an autoclave). This process also requires the removal of a resulting urea by-product that is formed from the dicyclohexylcarbodiimide coupling agent. Due to the challenges involved in the process of the '924 patent, there is clearly a need for a process for making valacyclovir that employs less severe deprotecting procedures and involves easier removal of by-products.

SUMMARY OF THE INVENTION

The present invention relates to a protected valacyclovir (N-t-BOC-valacyclovir) and a method of making it. The present invention further relates to a method of making valacyclovir or a pharmaceutically acceptable salt thereof including coupling and deprotecting (deblocking) steps. The present invention further relates to valacyclovir in pure form (pure valacyclovir), a method of making pure valacyclovir, and to compositions containing pure valacyclovir.

In one aspect, the present invention relates to N-tert-butoxycarbonyl-L-valine 2-[(2-amino-1,6-dihydro-6-oxo-9H-purin-9-yl)methoxy] ethyl ester (N-t-BOC-valacyclovir).

In another aspect, the present invention relates to a method of making N-t-BOC-valacyclovir including the step of coupling N-t-butoxycarbonyl valine with acyclovir in the presence of a coupling agent. In a particular aspect, the coupling agent is a carbodiimide, such as dicyclohexylcarbodiimide, or a water-soluble carbodiimide, such as N-(3-dimethylaminopropyl)-N-ethyl carbodiimide.

In another aspect, the present invention relates to a method of making valacyclovir including the steps of coupling an amine protected valine with acyclovir to form a protected valacyclovir and deprotecting the protected valacyclovir to form valacyclovir or a pharmaceutically acceptable salt thereof. Examples of amine protected valines include N-t-butoxycarbonyl valine and N-formyl valine. In a particular aspect, the coupling is effected with a coupling agent that is a carbodiimide, such as dicyclohexylcarbodiimide or N-(3-dimethylaminopropyl)-N-ethyl carbodiimide.

In another aspect, the present invention relates to a method of making valacyclovir hydrochloride including the steps of coupling an amine protected valine selected from N-t-butoxycarbonyl valine and N-formyl valine with acyclovir to form a protected valacyclovir, wherein the coupling is effected with a carbodiimide selected from dicyclohexylcarbodiimide and N-(3-dimethylaminopropyl)-N-ethyl carbodiimide, and deprotecting the protected valacyclovir with hydrochloric acid.

In another aspect, the present invention relates to a method of making valacyclovir hydrochloride in pure form including the steps of forming a slurry of valacyclovir hydrochloride in a lower alkyl alcohol, refluxing the slurry, and isolating pure valacyclovir from the slurry. Examples of suitable lower alkyl alcohols include $C_{1-6}$ alkyl alcohols. Ethanol is a preferred lower alkyl alcohol.

In another aspect, the present invention relates to a method of making valacyclovir hydrochloride in pure form including the steps of forming a slurry of valacyclovir hydrochloride in ethanol, refluxing the slurry, and isolating pure valacyclovir from the slurry.

In another aspect, the present invention relates to a method of making pure valacyclovir hydrochloride including the steps of: coupling an amine protected valine selected from N-t-butoxycarbonyl valine and N-formyl valine with acyclovir to form a protected valacyclovir, wherein the coupling is effected with a carbodiimide selected from dicyclohexylcarbodiimide and N-(3-dimethylaminopropyl)-N-ethyl carbodiimide; deprotecting the protected valacyclovir with hydrochloric acid to form valacyclovir hydrochloride; forming a slurry of valacyclovir hydrochloride in ethanol; refluxing the slurry; and isolating pure valacyclovir hydrochloride from the slurry.

In another aspect, the present invention relates to a method of making valacyclovir hydrochloride in pure form including the steps of forming a solution of valacyclovir hydrochloride in water, optionally filtering the solution, mixing the solution with isopropanol to form a slurry, and isolating valacyclovir hydrochloride in pure form from the slurry.

In yet another aspect, the present invention relates to a method of making pure valacyclovir hydrochloride including the steps of: coupling an amine protected valine selected from N-t-butoxycarbonyl valine and N-formyl valine with acyclovir to form a protected valacyclovir, wherein the coupling is effected with a carbodiimide selected from dicyclohexylcarbodiimide and N-(3-dimethylaminopropyl)-N-ethyl carbodiimide; deprotecting the protected valacyclovir with hydrochloric acid to form valacyclovir hydrochloride; forming a solution of valacyclovir hydrochloride in water; optionally filtering the solution; mixing the solution with isopropanol to form a slurry; and isolating the pure valacyclovir hydrochloride from the slurry.

In yet another aspect, the present invention relates to valacyclovir hydrochloride in pure form. In a particular aspect, the present invention relates to valacyclovir hydrochloride having between about 0.1% and about 0.7% (but not more than about 0.7%) acyclovir as determined by HPLC. In another particular aspect, the present invention relates to valacyclovir hydrochloride having less than about 0.3% acyclovir. In another particular aspect, the present invention relates to valacyclovir hydrochloride having less than about 0.1% acyclovir. In another particular aspect, the present invention relates to valacyclovir hydrochloride having less than about 0.2% of any impurity. In another particular aspect, the present invention relates to valacyclovir hydrochloride having less than about 0.1% of any impurity.

DETAILED DESCRIPTION OF THE INVENTION

As used herein in connection with a measured quantity, the term "about" indicates that variation in the measured quantity as would be expected by the skilled artisan making the measurement or determination and exercising a level of care commensurate with the objective of the measurement and the precision of the measuring apparatus being used.

As used herein, unless the context requires otherwise, the phrase "valacyclovir hydrochloride" includes anhydrous forms, hydrates, and solvates thereof.

When used in describing purity or in reference to an amount of an impurity, percent (%) refers to area percent of a chromatogram determined by high-pressure liquid chromatography (HPLC), also known as high-performance liquid chromatography, as described below and is calculated according to the equation:

% Impurity $i$=100×(Peak Area Impurity $i$)/($\Sigma$ Area of All Peaks)

Purity is determined by HPLC using an Inertsil ODS-3V 5 µm, 150×4.6 mm column (e.g. GL Sciences No. 5020-01731), employing acetonitrile/water (containing 0.4% $F_3CCOOH$ adjusted to pH 3.0 with triethylamine) gradient eluent (3% $CH_3CN$/97% water to 60% $CH_3CN$/40% water over 30 minutes) at 25° C., having a flow rate of 1 ml/minute. An ultraviolet detector at 254 nm is used.

Samples are prepared for HPLC analysis by preparing a mother solution having about 22 mg of sample dissolved in a diluent consisting of 3 volumes of acetonitrile and 97 volumes of 60% $CH_3CN$/40% water (i.e. the ending eluent described above), having a total solution volume of 25.0 ml. A 5 ml aliquot of the mother solution is diluted with the diluent to a total volume of 10.0 ml. The resulting solution is filtered through a 0.45 µm membrane filter. The nominal injection volume is 20 µl. Under these conditions, acyclovir has a retention time of about 4.95 minutes; valacyclovir has a retention time of about 8.20 minutes; the first impurity has a retention time of about 3.15 minutes; the second impurity has a retention time of about 9.10 minutes; and the third impurity has a retention time of about 12.05 minutes.

In one embodiment, the present invention provides N-t-BOC-valacyclovir. This protected valacyclovir can be prepared as discussed below by coupling N-t-butoxycarbonyl valine with acyclovir in the presence of a carbodiimide.

In another embodiment, the present invention provides a method of making protected N-t-BOC-valacyclovir including the step of coupling N-t-butoxycarbonyl valine and acyclovir in the presence of a carbodiimide.

In the coupling step of the present invention, the hydroxyl group of acyclovir (I) is esterified with a N-t- butoxycarbonyl-protected valine to form protected N-t-BOC-valacyclovir. Using techniques known in the art, the coupling step can be performed in solution, preferably in a dipolar aprotic solvent, most preferably in dimethylformamide, using a base catalyst, a coupling agent, and, optionally, an aliphatic amine such as triethyl amine. The preferred catalyst is 4-(dimethylamino)pyridine.

Without relying on any particular theory of operation, it is believed that the coupling agent forms an activated species, in situ, that is disposed to react with an alcoholic hydroxyl group to form an ester. Carbodiimides are structurally characterized by a —N=C=N— moiety and are an example of coupling agents useful in the practice of the present invention. Preferred coupling agents include dicyclohexylcarbodiimide and N-(3-dimethylaminopropyl)-N-ethyl carbodiimide, both of which are commercially available.

The protected N-t-BOC-valacyclovir of the present invention differs from valacyclovir in that the amino group of the valine moiety bears a blocking N-t-BOC substituent. The protected valacyclovir can be converted into valacyclovir or a pharmaceutically acceptable salt thereof by removing the protecting group in the deprotecting step of the present invention.

In another embodiment, the present invention provides a method of making valacyclovir including the steps of coupling an amine protected valine with acyclovir to form a protected valacyclovir and deprotecting the protected valacyclovir to form valacyclovir or a pharmaceutically acceptable salt thereof. The coupling step is preferably effected with a coupling agent that is a carbodiimide such as dicyclohexylcarbodiimide and N-(3-dimethylaminopropyl)-N-ethyl carbodiimide.

As discussed above, an amine protected valine is an N-substituted 2-amino-3-methyl butanoic acid in which the substituent blocks the amino group from participating in or interfering or competing with the coupling reaction of the present invention, but which can be removed from the amino group after the coupling reaction. Preferred amine protected valines include N-t-butoxycarbonyl valine and N-formyl valine. N-t-Butoxycarbonyl valine is a particularly preferred amine protected valine.

When either N-t-butoxycarbonyl valine or N-formyl valine are used as the amine protected valine, the deprotecting step can be carried out under mild conditions using, for example, about a one to ten fold excess (based on moles of protected valacyclovir to be deprotected) of a mineral acid. A preferred mineral acid is aqueous hydrochloric acid. When the deprotecting step is carried out with aqueous hydrochloric acid, the product of the deprotecting step is valacyclovir hydrochloride, a pharmaceutically acceptable salt of valacyclovir. The deprotecting step can also be carried out with the protected valacyclovir in solution or, preferably, in aqueous suspension, with or without the addition of an organic solvent such as acetone, acetic acid, ethanol, isopropanol, formic acid, or mixtures thereof.

When deprotecting with aqueous hydrochloric acid is carried out in suspension, aqueous hydrochloric acid (2–10N) is added dropwise to a suspension of valacyclovir in water, typically 2 ml/gram of protected valacyclovir. The valacyclovir hydrochloride can be precipitated from the solution that ultimately forms by mixing the solution with isopropanol (typically about 4–8 volumes/volume of solution). The precipitated product can be recovered by any technique known to one skilled in the art of synthetic organic chemistry, for example by filtration (gravity or suction) or centrifugation. Preferably, the recovered product is dried in vacuo.

Preferably, the deprotecting step is carried out at a temperature of from about −10° C. to about 50° C., more preferably about −10° C. to about 25° C., and most preferably about 20° C. to about 25° C.

In another embodiment, the present invention provides a method of making valacyclovir hydrochloride in pure form. Valacyclovir hydrochloride, prepared as described above or by any other method, can be purified to pure valacyclovir hydrochloride by subjecting it to the suspension method of the present invention. The suspension method of the present invention includes the steps of forming a slurry of valacyclovir hydrochloride in a lower alkyl alcohol, refluxing the slurry, and after refluxing, isolating pure valacyclovir hydrochloride from the slurry. Examples of suitable lower alkyl alcohols include $C_{1-6}$ alkyl alcohols. Ethanol is a preferred lower alkyl alcohol.

To form the slurry, valacyclovir hydrochloride is combined with a lower alkyl alcohol, for example ethanol, (about 25 to 100 ml/gram of solid) in a suitable vessel. A suitable vessel will provide for agitating the slurry and condensing and returning the lower alkyl alcohol in the reflux step. Flasks and tank reactors equipped with agitators and condensers are known suitable vessels. The skilled artisan will select the means of agitation (for example magnetic stirrer, overhead paddle, propeller, or turbine stirrer) and condensing apparatus according to the size and design of the vessel.

In preferred embodiments, the slurry is stirred at a temperature of from about 20° C. to about 30° C. for about 15 minutes to about 2 hours. The slurry is then heated to reflux. The skilled artisan will know to adjust the time of the reflux step according to, among other things, the initial purity of the valacyclovir hydrochloride, the desired level of purity in the final product, and the characteristics of the equipment being used. If desired, the purity can be checked by removing an aliquot of the mixture from the vessel, cooling it to about 25° C. or below, and analyzing the solid obtained according to the HPLC procedure described above. A reflux time of about 15 minutes to about 2 hours is typical. When the valacyclovir hydrochloride is made by the coupling and deprotecting method of the present invention, a reflux time of about 1 hour is generally sufficient.

Following reflux, the contents of the vessel are cooled to about 25° C. or less and stirred for about 15 minutes to about 1 hour. The solid is recovered from the resulting slurry by any means known to the skilled artisan. The recovered solid is then dried, preferably in vaco at a temperature of from about 30° C. to about 80° C., preferably at about 40° C., to obtain valacyclovir hydrochloride in pure form.

In another embodiment, the present invention provides valacyclovir hydrochloride in pure form. Valacyclovir hydrochloride in pure form obtained by the suspension method of the present invention can contain first, second, and third impurities, in addition to acyclovir. The level of acyclovir and first, second, and third impurities can be determined by the HPLC method described above. The skilled artisan will understand that first, second, and third impurities can include more than one chemical species having the approximate retention times recited in the HPLC method described above. Valacyclovir hydrochloride in pure form can include from about 0.1% up to about 0.5% each of first, second, and third impurities and, in a preferred embodiment, includes between about 0.1% and 0.3% each of first, second, and third impurities.

Most preferably, valacyclovir hydrochloride includes not more than about 0.1% each of first second, and third impurities. Pure valacyclovir hydrochloride will have not more than about 0.7%, preferably between about 0.1% and about 0.3% but not more than 0.5%, and most preferably not more than about 0.1% acyclovir. Pure valacyclovir hydrochloride will have not more than about 0.2% of any impurity, and preferably not more than about 0.1% of any impurity.

Pure valacyclovir hydrochloride, which is obtained as a powder, can be milled into a finer powder. The powder can be used in a pharmaceutical product or physically modified such as by granulation to produce larger granules. Pure valacyclovir hydrochloride is useful for treating patients with herpes zoster and genital herpes. Pure valacyclovir hydrochloride can be formulated into a variety of compositions for administration to patients in need thereof.

Valacyclovir hydrochloride, prepared as described above or by any other method, can also be purified to pure valacyclovir hydrochloride by subjecting it to the solution method of the present invention. The solution method of the present invention includes the steps of forming a solution of valacyclovir hydrochloride in water, optionally filtering the resulting solution, mixing the solution with isopropanol to form a slurry, and isolating the pure valacyclovir hydrochloride from the slurry.

To form the solution, valacyclovir hydrochloride is combined with water in a suitable vessel. In a preferred embodiment, the solution is stirred at a temperature of from about 20° C. to about 50° C. for about 15 minutes to about 4 hours. After filtering the solution, isopropanol is added at a temperature of from about 0° C. to about 10° C. and stirred at about 20° C. for a holding time sufficient to form a slurry. A holding time of up to about 12 hours is sufficient. The solid can be recovered from the resulting slurry and dried by any means known to the skilled artisan as discussed above.

Pharmaceutical compositions of the present invention contain pure valacyclovir hydrochloride. In addition to the active ingredient, the pharmaceutical compositions of the present invention can contain one or more excipients. Excipients are added to the composition for a variety of purposes.

Diluents increase the bulk of a solid pharmaceutical composition and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form like a tablet can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flow properties of non-compacted solid composition and improve the accuracy of dosing. Excipients that can function as glidants include colloidal silicon dioxide, magnesium trisilicate, powdered cellulose, starch, talc and tribasic calcium phosphate.

When a dosage form such as a tablet is made by compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease release of the product form the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Selection of excipients and the amounts to use can be readily determined by the formulation scientist based upon experience and consideration of standard procedures and reference works in the field.

The solid compositions of the present invention include powders, granulates, aggregates and compacted compositions.

Pure valacyclovir hydrochloride can be administered to a patient in oral unit dosage form. The active ingredient and excipients can be formulated into compositions and dosage forms according to methods known in the art. Dosage forms include solid dosage forms like tablets, powders, capsules, sachets, troches and lozenges as well as liquid syrups, suspensions and elixirs.

A composition for tableting or capsule filing can be prepared by wet granulation. In wet granulation some or all of the active ingredients and excipients in powder form are blended and then further mixed in the presence of a liquid, typically water, that causes the powders to clump up into granules. The granulate is screened and/or milled, dried and then screened and/or milled to the desired particle size. The granulate can then be tableted or other excipients can be added prior to tableting such as a glidant and/or lubricant.

A tableting composition can be prepared conventionally by dry blending. For instance, the blended composition of the active ingredient and excipients can be compacted into a slug or a sheet and then comminuted into compacted granules. The compacted granules can be compressed subsequently into a tablet.

As an alternative to dry granulation, a blended composition can be compressed directly into a compacted dosage form using direct compression techniques. Direct compression produces a more uniform tablet without granules. Excipients that are particularly well suited to direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, only they are not subjected to a final tableting step.

A capsule can, for example, be prepared by filling half of a gelatin capsule with the above tablet composition and capping it with the other half of the gelatin capsule.

Capsules, tablets and lozenges and other unit dosage forms preferably contain a dosage level of about 100 mg to about 1000 mg, more preferably from about 500 mg to about 1000 mg of pure valacyclovir hydrochloride.

The present invention is further illustrated by the following examples.

EXAMPLE 1

N-t-BOC-Valacyclovir (N-tert-Butoxycarbonyl-L-valine 2-[(2-amino-1,6-dihydro-6-oxo-9H-purin-9-yl)methoxy] Ethyl Ester)

A suspension of N-t-BOC-L-valine (2.9 g, 13.2 mmol), acyclovir (2.3 g, 10 mmol), 1-(3-dimethylaminopropyl)-3-ethylcarbodiimide hydrochloride (3.0 g, 15 mmol), 4-(dimethylamino)pyridine (0.2 g, 1.6 mmol) and triethylamine (1.4 g, 13.9 mmol) in dimethylformamide (15 mL) was stirred for about 4 hours at about 0° C. and overnight at room temperature. An additional amount of N-t-BOC-L-valine (0.3 g, 1.36 mmol) and 1-(3-dimethylaminopropyl)-3-ethylcarbodiimide hydrochloride (0.3 g, 1.5 mmol) were added to the reaction mixture, and stirring was continued overnight. A solution of 0.3 N hydrochloric acid (53 mL) was added to a clear solution at about 0° C., a white precipitate formed and the suspension was stirred at about 0° C. for about 1 hour. The precipitate was filtered and dried under reduced pressure to give N-t-BOC-valacyclovir (4.1 g, 97%) with 98.2% purity by HPLC.

1H NMR (DMSO-d6, d, ppm): 0.79 (d, J=6.6 Hz, 6H); 1.35 (s, 9H); 1.80–2.00 (m, 1H); 3.60–3.80 (m, 2H); 4.00–4.30 (m, 2H), 5.33 (s, 2H); 6.49 (s, 2H); 7.11 (d, J=7.9); 7.79 (s, 1H); 10.63 (s, 1H).

EXAMPLE 2

N-t-BOC-Valacyclovir (N-tert-Butoxycarbonyl-L-valine 2-[(2-amino-1,6-dihydro-6-oxo-9H-purin-9-yl)methoxy] Ethyl Ester)

A double-jacketed reactor (1 L) was charged with acyclovir (50.00 g), N-t-BOC-L-valine (72.35 g), 4-(dimethylamino)pyridine (4.07 g) and N,N-dimethylformamide (210.0 g) and filled with nitrogen. The mixture was stirred for about 1 hour at about 25° C., and then cooled to about 20° C. A solution of 1,3-dicyclohexylcarbodiimide (91.61 g) in N,N-dimethylformamide (160 g) was added dropwise to the reaction mixture at about 20–25° C. The reaction mixture was stirred for about 2 hours at about 25° C. with vigorous stirring. Afterward water (17.0 g) was added to the reaction mixture and then it was stirred for about 12 hours at about 20–25° C. A precipitate was filtered and washed on the filter with N,N-dimethylformamide (150.0 g). The filtrate was concentrated to about 235 g under reduced pressure at about 65° C. At about 60–65° C., methanol (280 g) was added dropwise to the stirred residue. The resulting solution was stirred for about 15 minutes under reflux conditions and for about 12 hours at about 0° C. The precipitated solid was filtered, washed on the filter with cold methanol (150.0 g) and dried under reduced pressure at 50° C. (water bath) to a constant weight to give N-t-BOC-valacyclovir (70.70 g, 75%) with 99.7% purity by HPLC.

EXAMPLE 3

N-t-BOC-Valacyclovir (N-tert-Butoxycarbonyl-L-valine 2-[(2-amino-1,6-dihydro-6-oxo-9H-purin-9-yl)methoxy] Ethyl Ester)

A double-jacketed reactor (6 L) was charged with N-t-BOC-L-valine (435.0 g, 2.002 mmol) and dimethylformamide (2790 g) and filled with nitrogen. The mixture was stirred for about 30 minutes at about 25° C., and then cooled to about –5° C. A solution of 1,3-dicyclohexylcarbodiimide (165.0 g, 2.660 mmol) in N,N-dimethylformamide (300 g) was added over about 20 minutes. The resulting mixture was stirred for about 30 minutes at about –5° C. and acyclovir (300.0 g, 1.332 mmol) was added over about 5 minutes at this temperature. In one portion, 4-(dimethylamino)pyridine (162.0 g, 1.327 mmol) was added at about –5° C. and then the mixture was stirred for about 6 hours at this temperature.

A new portion of 1,3-dicyclohexylcarbodiimide (165.0 g) in N,N-dimethylformamide (300 g) was added dropwise to the mixture at about –5° C., which was stirred for about 13 hours at this temperature.

The last portion of 1,3-dicyclohexylcarbodiimide (219.0 g) in N,N-dimethylformamide (390 g) was added dropwise to the mixture at about –5° C. and stirring continued for about 6 hours at this temperature. Then the temperature was increased to about 25° C. for about 15 hours. After, water (102 g, 5.667 mmol) was added to the mixture and stirring continued for about 3 hours at about 25° C. A precipitate was filtered and washed with N,N-dimethylformamide (900 g). The filtrate was concentrated under reduced pressure at about 65° C. The residue was dissolved under reflux in isopropanol (900 g) and dried under reduced pressure at about 40–50° C. (water bath) to a constant weight to give N-t-BOC-valacyclovir (486 g, 86%) with 97.5% purity by HPLC.

EXAMPLE 4

Valacyclovir Hydrochloride from N-t-BOC-Valacyclovir

A solution of 5N hydrochloric acid (7 mL) was added dropwise to a suspension of N-t-BOC-valacyclovir (3.4 g, 8 mmol) in water (11 mL) and stirred for about 5 hours at room temperature, during this time the suspension disappeared and a clear solution formed. The solution was cooled to about 0° C. and mixed with isopropanol (60 mL), after which a precipitate formed. The resulting suspension was stirred for about 1 hour at about 0° C. and kept overnight at about 4° C. A white precipitate was filtered and dried under reduced pressure to afford valacyclovir hydrochloride (1.8 g, 62%).

1H NMR corresponded to the previously disclosed NMR for valacyclovir hydrochloride.

EXAMPLE 5

Valacyclovir Hydrochloride from N-t-BOC-Valacyclovir

A solution of 12N hydrochloric acid (8 mL, 96 mmol) was added dropwise to a suspension of N-t-BOC-valacyclovir (9.0 g, 21 mmol) in water (22 mL) and stirred for about 3.5 hours at room temperature, during this time the suspension disappeared and a turbid solution formed. The solution was cooled to about 0° C. and mixed with isopropanol (500 mL), after which a precipitate formed. The resulting suspension was stirred for about 1 hour at about 0° C. and kept overnight at about 4° C. A white precipitate was filtered and dried under reduced pressure at about 40–50° C. to a constant weight to afford valacyclovir hydrochloride (7.0 g, 92%) with 97.9% purity by HPLC.

Valacyclovir hydrochloride (2.0 g) was triturated with ethanol (100 mL) for about 1 hour under reflux conditions and was then cooled to room temperature. The white precipitate was filtered and dried under reduced pressure at about 40–50° C. to a constant weight to give valacyclovir hydrochloride (1.3 g, 65%) having 99.27% purity by HPLC.

EXAMPLE 6

Valacyclovir Hydrochloride from N-t-BOC-Valacyclovir

A double-jacketed reactor (1 L) was charged with N-t-BOC-valacyclovir (100.0 g, 235.6 mmol) and formic acid (300.0 g). The resulting mixture was stirred at about 50° C. to complete dissolution of the solids and then was cooled to about 20–25° C. A mixture of 37% hydrochloric acid (92.8 g) and water (200 g) was added dropwise over a period of about 1 hour and the solution was stirred for another 3 hours at about 20–25° C. The reaction mixture was filtered and the filtrate was added dropwise over a period of 1 hour to isopropanol (1256 g) at about 20° C. The resulting suspension was stirred for about 2 hours at the same temperature and for about 14 hours at about −15° C. The precipitated solid was filtered, washed with cold isopropanol (400 g) and dried under reduced pressure at about 25° C. to a constant weight to give valacyclovir hydrochloride (62.5 g, 73.5%) with 98.67% purity by HPLC.

EXAMPLE 7

Valacyclovir Hydrochloride in Pure Form

A solution of 12N hydrochloric acid (8.0 mL, 96 mmol, 4.6 eq) was added dropwise to a slurry of N-t-BOC-valacyclovir (9.0 g, 21 mmol, 1 eq) in water (22 mL) at about 20–25° C. and stirred for about 3.5 hours at the same temperature. During this time the slurry disappeared and an oily solution formed. Isopropanol (500 mL) was added to the stirred solution at about 0–5° C. The resulting suspension was stirred overnight at the same temperature. The precipitated solid was filtered off and dried under reduced pressure at about 20–30° C. to constant weight to give valacyclovir hydrochloride (7.0 g, 92%) in 97.93% purity by HPLC; dicyclohexyl urea <0.1% and between about 0.1% and 0.2% unreacted N-t-BOC-valine (estimated by TLC).

Valacyclovir hydrochloride (2.0 g) was stirred with ethanol (100 mL) for about 1 hour under reflux conditions and for about 30 minutes at room temperature. The suspension was filtered and dried under reduced pressure at about 40° C. to give valacyclovir hydrochloride (1.3 g, 65%) having 99.27% purity by HPLC.

EXAMPLE 8

Valacyclovir Hydrochloride in Pure Form

A reactor (1 L) was charged with crude valacyclovir hydrochloride (60.00 g) and water (240 g). The resulting mixture was stirred at about 40° C. to complete dissolution of the solids and the solution was filtered. The filtrate was added to isopropanol (900 g) at about 40° C. and the resulting suspension was stirred for about 2 hours at about 20° C. and for another 17 hours at about −15° C. The precipitated solid was filtered, washed with cold isopropanol (120 g) and dried under reduced pressure at about 25° C. to a constant weight to give valacyclovir hydrochloride (53.24 g, 88.7%) with 99.56% purity by HPLC.

We claim:

1. N-tert-butoxycarbonyl-L-valine 2-[(2-amino-1,6-dihydro-6-oxo-9H-purin-9-yl)methoxy] ethyl ester.

2. A method of making N-tert-butoxycarbonyl-L-valine 2-[(2-amino-1,6-dihydro-6-oxo-9H-purin-9-yl)methoxy] ethyl ester comprising the step of coupling N-t-butoxycarbonyl valine with acyclovir in the presence of coupling agent.

3. The method of claim 2 wherein the coupling agent is a carbodiimide.

4. The method of claim 3 wherein the carbodiimide is dicyclohexylcarbodiimide.

5. The method of claim 3 wherein the carbodiimide is water-soluble.

6. The method of claim 5 wherein the water-soluble carbodiimide is N-(3-dimethylaminopropyl)-N-ethyl carbodiimide.

7. A method of making valacyclovir or a pharmaceutically acceptable salt thereof comprising the steps of:
coupling an amine protected valine selected from N-t-butoxycarbonyl valine and N-formyl valine with acyclovir to form a protected valacyclovir, and
deprotecting the protected valacyclovir to form valacyclovir or a pharmaceutically acceptable salt thereof.

8. The method of claim 7 wherein the amine protected valine is N-t-butoxycarbonyl valine.

9. The method of claim 7 wherein the coupling is effected with a coupling agent.

10. The method of claim 9 wherein the coupling agent is a carbodiimide.

11. The method of claim 10 wherein the carbodiimide is dicyclohexylcarbodiimide.

12. The method of claim 10 wherein the carbodiimide is water soluble.

13. The method of claim 12 wherein the water-soluble carbodiimide is N -(3-dimethylaminopropyl)-N-ethyl carbodiimide.

14. The method of claim 7 wherein the deprotecting is effected at a temperature of from about 20° C. to about 25° C.

15. The method of claim 7 wherein the deprotecting is effected in a solvent selected from the group consisting of acetone, acetic acid, formic acid, and mixtures thereof.

16. The method of claim 7 wherein the deprotecting is effect with a mineral acid.

17. The method of claim 16 wherein the mineral acid is hydrochloric acid and valacyclovir hydrochloride is formed.

18. A method of making valacyclovir hydrochloride comprising the steps of:
coupling an amine protected valine selected from N-t-butoxycarbonyl valine and N-formyl valine with acyclovir to form a protected valacyclovir, where the coupling is effected with a coupling agent selected from N-(3-dimethylaminopropyl)-N-ethyl carbodiimide and dicyclohexylcarbodiimide, and deprotecting the protected valacyclovir with hydrochloric acid.

19. The method of claim 18 wherein the amine protected valine is N-t-butoxycarbonyl valine.

20. The method of claim 18 wherein the deprotecting is effected at a temperature of from about 20° C. to about 25° C.

21. The method of claim 18 wherein the deprotecting is effected in a solvent selected from the group consisting of acetone, acetic acid, formic acid, and mixtures thereof.

22. The method of claim 2 wherein the coupling is conducted at about 0° C.

23. The method of claim 2 wherein the coupling is at a temperature of about −5° C.

24. The method of claim 2 wherein the coupling is at a temperature of about 25° C.

* * * * *

UNITED STATES PATENT AND TRADEMARK OFFICE
CERTIFICATE OF CORRECTION

PATENT NO. : 6,849,737 B2
DATED : February 1, 2005
INVENTOR(S) : Etinger et al.

It is certified that error appears in the above-identified patent and that said Letters Patent is hereby corrected as shown below:

Column 6,
Line 47, change "vaco" to -- vacuo --

Column 8,
Lines 15, 17 and 20, change "dye" to -- die --

Signed and Sealed this

Ninth Day of August, 2005

JON W. DUDAS
*Director of the United States Patent and Trademark Office*